United States Patent [19]
Jeffers et al.

[11] Patent Number: 5,629,620
[45] Date of Patent: May 13, 1997

[54] APPARATUS AND METHOD FOR MEASUREMENT OF MAGNETIC REMANENCE-THICKNESS PRODUCT OF THIN MAGNETIC LAYERS

[75] Inventors: Frederick J. Jeffers, Escondido; Neil Smith, San Diego, both of Calif.

[73] Assignee: Eastman Kodak Company, Rochester, N.Y.

[21] Appl. No.: 398,197

[22] Filed: Mar. 2, 1995

[51] Int. Cl.⁶ .......................... G01R 33/12; G01N 27/76
[52] U.S. Cl. .......................................... 324/210; 324/235
[58] Field of Search .................................. 324/228, 235, 324/239, 240, 243, 225, 210, 211, 212, 207.12, 207.21, 252, 207.26; 360/31, 123; 365/201; 346/33 M

[56] References Cited

U.S. PATENT DOCUMENTS

| | | | |
|---|---|---|---|
| 3,535,622 | 10/1970 | Cannon et al. | 324/212 |
| 3,562,635 | 2/1971 | Parker | 324/212 |
| 4,038,692 | 7/1977 | Umeda et al. | 360/65 |
| 4,182,985 | 1/1980 | DeWolfe et al. | 324/235 X |
| 4,213,091 | 7/1980 | Cooper | 324/210 |
| 4,276,324 | 6/1981 | Pohler et al. | 324/212 |
| 4,603,365 | 7/1986 | Nakamura | 324/225 X |
| 4,901,016 | 2/1990 | Kusatani et al. | 324/210 |
| 5,351,005 | 9/1994 | Rouse et al. | 324/225 X |

OTHER PUBLICATIONS

IBM Technical Bulletin, vol. 6, No. 8, Jan. 1964 pp. 48–49.

*Primary Examiner*—Sandra L. O'Shea
*Assistant Examiner*—Roger C. Phillips
*Attorney, Agent, or Firm*—William F. Noval

[57] ABSTRACT

In the simplest embodiment of the invention, the apparatus holds the edge of the magnetized film to be measured close to, and above, a linearly biased magnetoresistive (MR) element. Magnetic poles appearing at the magnetic discontinuity at the edge of the film generate a magnetic field which is incident on the MR element, and which results in a measurable change in the element's resistivity. In a preferred embodiment, a pair of MR elements are placed so that they are both linearly biased by a magnet; only one of the MR elements being in close proximity to, and influenced by the magnetic field emanating from the edge of the magnetized film. The second MR element, selected for matched characteristics with the first MR element, is located out of the field of the magnetized film, but still subject to the same temperature environment and field noise as the first MR element. The two MR elements are configured with associated resistors as arms of a Wheatstone bridge so that the common mode fields and thermal drift signals experienced by both MR elements are canceled to the first order, and the output of the bridge is proportional to the change in resistance in the first MR element due only to the field of the magnetized film.

3 Claims, 3 Drawing Sheets

APPARATUS AND METHOD FOR MEASUREMENT OF MAGNETIC REMANENCE-THICKNESS PRODUCT OF THIN MAGNETIC LAYERS

BACKGROUND OF THE INVENTION

1. Field of the Invention

This invention relates to apparatus and method for magnetic measurement, and in particular to measurment of the magnetic remanence-thickness product of a thin magnetic layer.

2. Description Relative to the Prior Art

The measurement of the magnetic remanence of a magnetically recorded layer is an important parameter in determining the recording effectiveness of the magnetic layer. In the prior art, measurement of the magnetic remanence of a recorded medium has conventionally been accomplished by use of a B-H loop tester which allows the determination of the remanent magnetization $M_r$. This method is described in U.S. Pat. No. 4,901,016 issued to Kusutani et al entitled "Device Having a Magnetic Head for Measuring Magnetization Characteristics of a Magnetic Thin Film" (Column 1 and Column 2, lines 1–47). As applied to determining the magnetic remanence of a thin film magnetic strip, they point out the necessity of using a sample consisting of about 10 layers of the magnetic film to provide sufficient magnetic material for the measurement, and that this method of measuring the remanence of a thin film strip is extremely cumbersome.

For thin recorded layers, the product of the magnetic remanence, $M_r$, times the layer thickness, $\delta$, is generally considered a more useful parameter in evaluating the recording effectiveness of a magnetic layer than the remanence alone. The $M_r\delta$ product measures the magnetic flux carrying capacity per unit width for a magnetized layer, and where, as is generally practiced in recording data, the recorded information is laid down in the form of tracks the $M_r\delta$ product is directly related to the flux strength/unit track width, and hence to the effectiveness of the medium for recording.

Generally the $M_r\delta$ product is small and difficult to measure accurately. For example, in a hard disk drive, the thickness of the magnetic film may be 750 angstroms and the remanent magnetization may be on the order of 500 emu/$cm^3$, resulting in the small value of the $M_r\delta$ product of $4\times10^{-3}$ emu/$cm^2$. In the present invention, apparatus is disclosed for measuring the $M_r\delta$ product of such magnetized thin film material in an accurate and repeatable manner.

SUMMARY OF THE INVENTION

In the simplest embodiment of the invention, the apparatus holds the edge of the magnetized film to be measured close to, and above, a linearly biased magnetoresistive (MR) element. Magnetic poles appearing at the magnetic discontinuity at the edge of the film generate a magnetic field which is incident on the MR element, and which results in a measurable change in the element's resistivity. In a preferred embodiment, a pair of MR elements are placed so that they are both linearly biased by a magnet; only one of the MR elements being in close proximity to, and influenced by the magnetic field emanating from the edge of the magnetized film. The second MR element, selected for matched characteristics with the first MR element, is located out of the field of the magnetized film, but still subject to the same temperature environment and field noise as the first MR element. The two MR elements are configured with associated resistors as arms of a Wheatstone bridge so that the common mode fields and thermal drift signals experienced by both MR elements are canceled to first order, and the output of the bridge is proportional to the change in resistance in the first MR element due only to the field of the magnetized film.

BRIEF DESCRIPTION OF THE DRAWINGS

The invention will be described with respect to the drawings of which.

DESCRIPTION OF THE PREFERRED EMBODIMENTS

Figure 1:
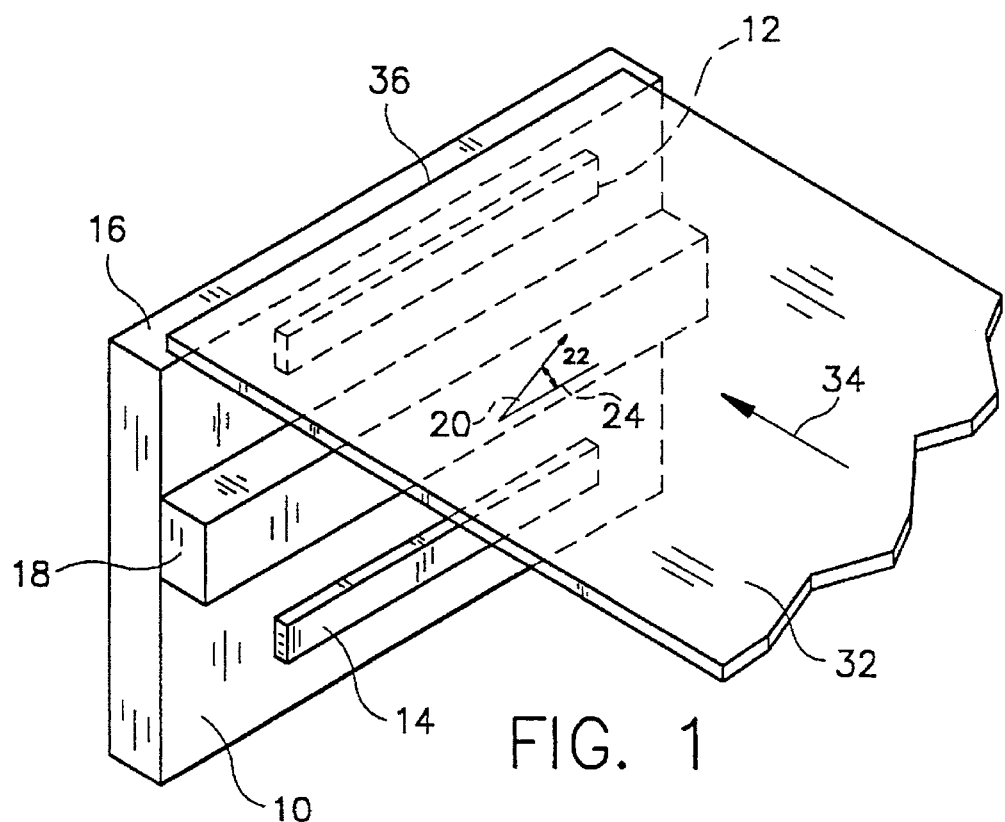
FIG. 1 schematically illustrates the configuration of the apparatus of the invention.
Figure 2:
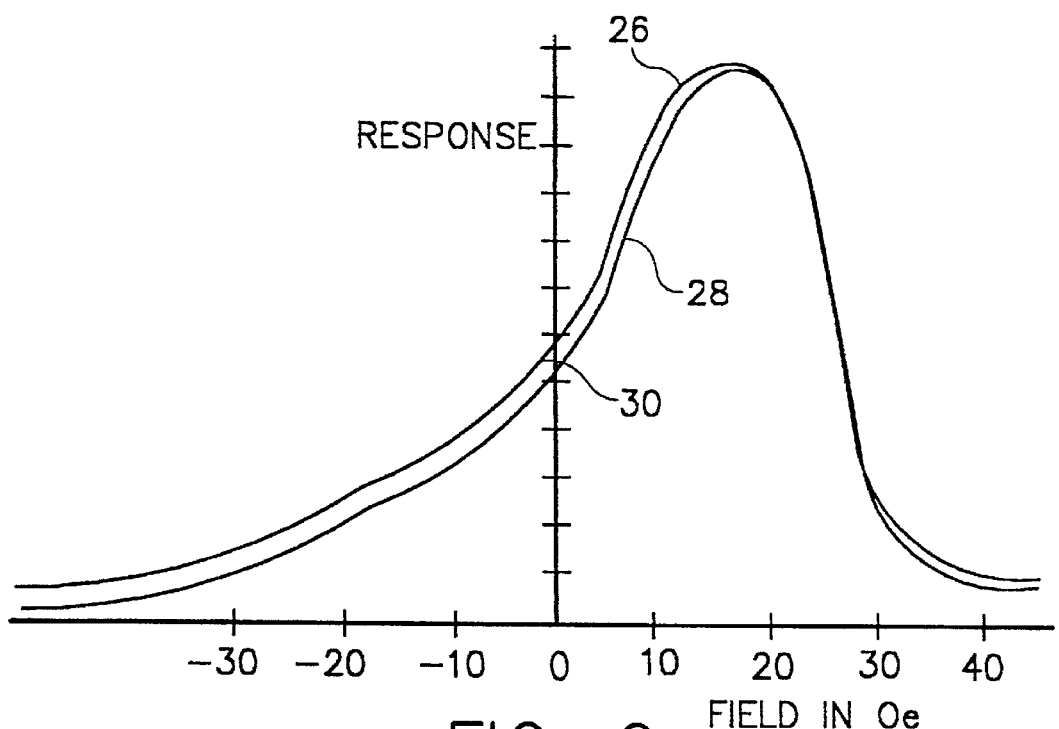
FIG. 2 is a drawing of the response functions of the MR elements used in the invention.

Referring to FIG. 1, a plate 10 has planar, rectangular MR elements 12,14 mounted thereon, with the MR element 12 close to an edge face, e.g. 16, of the plate 10, and the MR element 14 mounted parallel to MR element 12 and approximately 300 mils distant from the MR element 12. Situated between the MR elements 12, 14 is a bar magnet 18, which may be fabricated from barium ferrite, and having its magnetization 20 at an angle 22 of about 15 degrees with the longitudinal direction 24 of the bar magnet 18. The long axes of the rectangular MR elements 12, 14 also are oriented along the same longitudinal direction 24. The magnetization 20 therefor has a field component at the MR elements 12, 14 perpendicular to the long axes of the MR elements 12,14 which linearly biases the MR elements 12,14. The MR elements 12,14 are geometrically congruent, and are selected for substantially identical magnetoresistive characteristics. In FIG. 2, it may be seen that the response curve 26 of the MR 12, and the response curve 28 of the MR 14 to an applied magnetic field are substantially the same. For zero applied field applied along the short dimension of the MR elements 12,14, both MR 12 and MR 14 are biased at point 30 which is on the linear and steepest portions of the response curves 26,28. Additionally, the longitudinal field of the magnetization 20, along the longitudinal direction of the MR elements 12,14, maintains the MR elements in a single domain state minimizing Barkhausen noise arising from domain wall movement in the MR elements 12,14.

Figure 3:
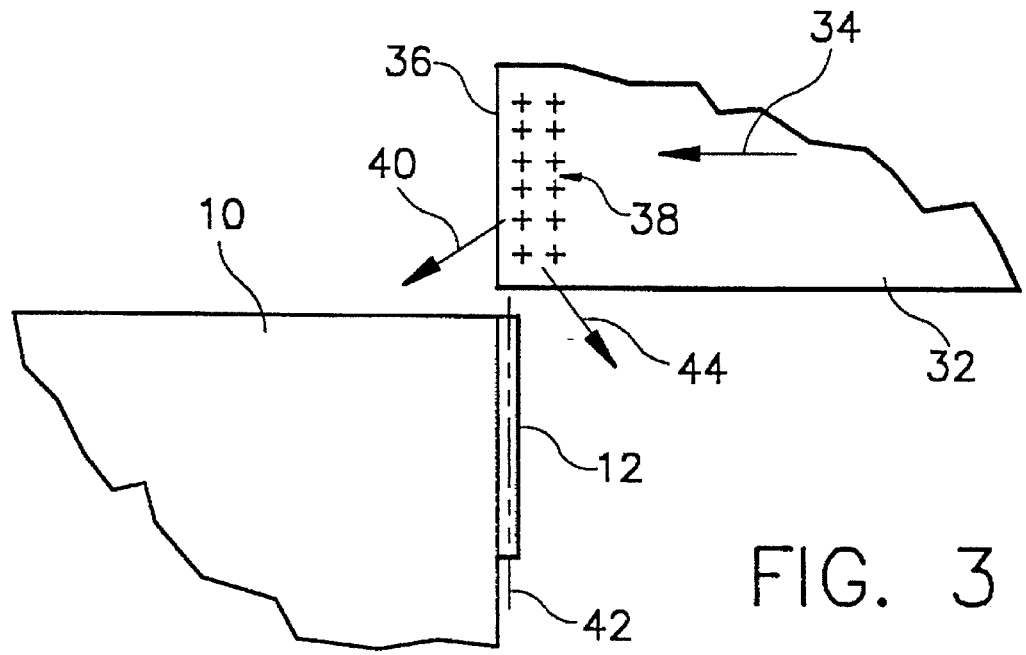
FIG. 3 is an expanded drawing useful in understanding of the invention.

A thin magnetic film sample 32, whose remanence-thickness product is to be measured, is magnetized to saturation with its magnetization 34 lying perpendicular to an edge 36 of the film sample 32 and in the plane of the film (FIG. 2). The magnetic film sample 32 may be readily magnetically saturated by exposing its surface to the 3000 Oe field of a NdFeB magnet. The film sample 32 is placed in close proximity to the MR element 12 so that its edge 36 is directly over the MR element 12 as shown in FIG. 3. The discontinuity of the magnetization 34 at the edge 36 results in magnetic charges 38 appearing at the edge 36. The magnetic charges 38 give rise to a magnetic field having components, e.g. 40,42,44 of which the component 42 is seen traversing the MR 12. The magnetic field intensity at the MR 12 is proportional to the amount of charge 38, which, in turn, is directly proportional to the remanence-thickness product of the magnetized film 32.

Figure 4:
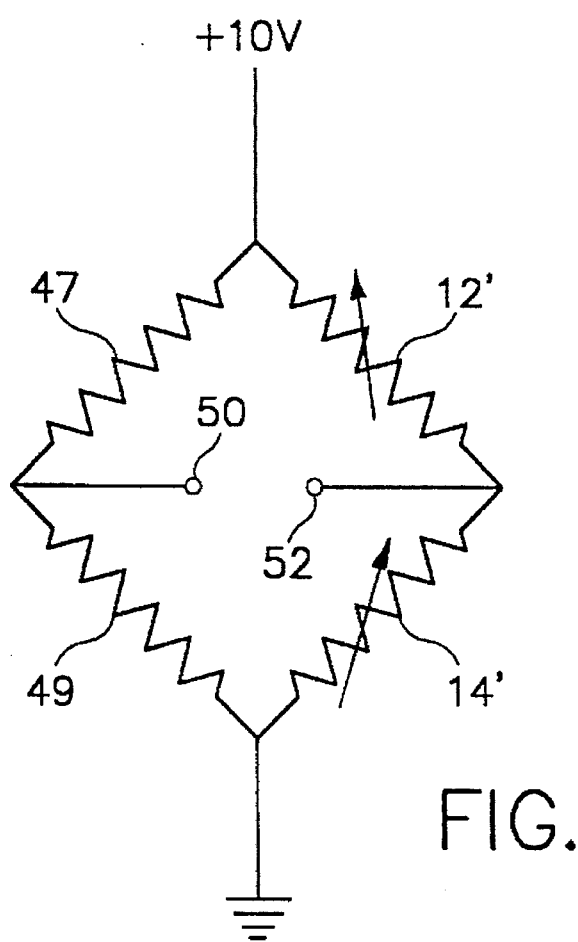
FIG. 4 is a schematic drawing of elements of the invention in a Wheatstone bridge.

Referring to FIG. 4, the MR element 12 having a resistance 12', and the MR element 14 having a resistance 14' are configured as two elements of a Wheatstone bridge. Resistances 47, 49 complete the bridge, and are chosen so that with no magnetic field incident on MR 12 the bridge is balanced, i.e. there is no potential between the terminals 50,52. (In the figures, different but related elements are designated by the same reference character, albeit they are distinguished by means of primes.) When measuring the $M_r\delta$ product of the film 32, it is positioned relative to the location of the MR element 12 seen in FIG. 3, and the magnetic field component, e.g. 42, causes a resistance change in the MR element 12 in accordance with the response curve 26 (FIG. 2). This resistance change results in a bridge output signal measured between the terminals 50,52 which may be detected by a strip chart recorder or by other means known in the art.

The signal field from the magnetized film 32 rapidly falls off with distance, and is sensed only by MR 12 and not by MR 14 which is 300 mils away from the edge 36. However, the Wheatstone bridge configuration causes the common mode fields such as interfering electromagnetic noise and thermal drift which affect both MR 12 and MR 14 to be canceled to first order. This greatly increases the signal-to-noise ratio (SNR) for the very small signals generated by the charges 38 at the edge 36 of the magnetized thin film 32.

Figure 5:
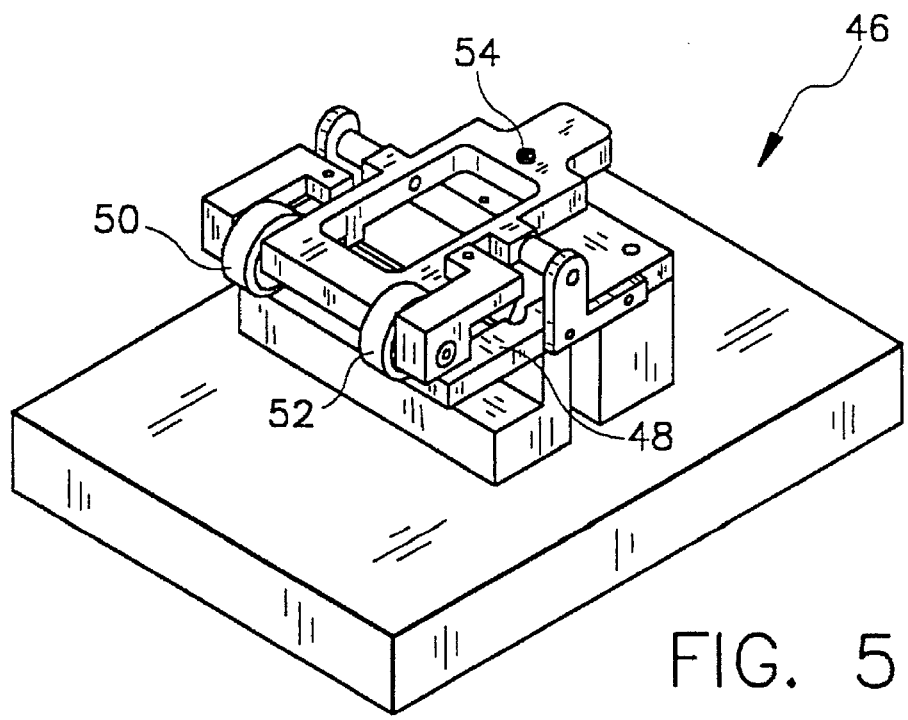
FIG. 5 is a drawing a fixture for holding a magnetic film.
Figure 6:
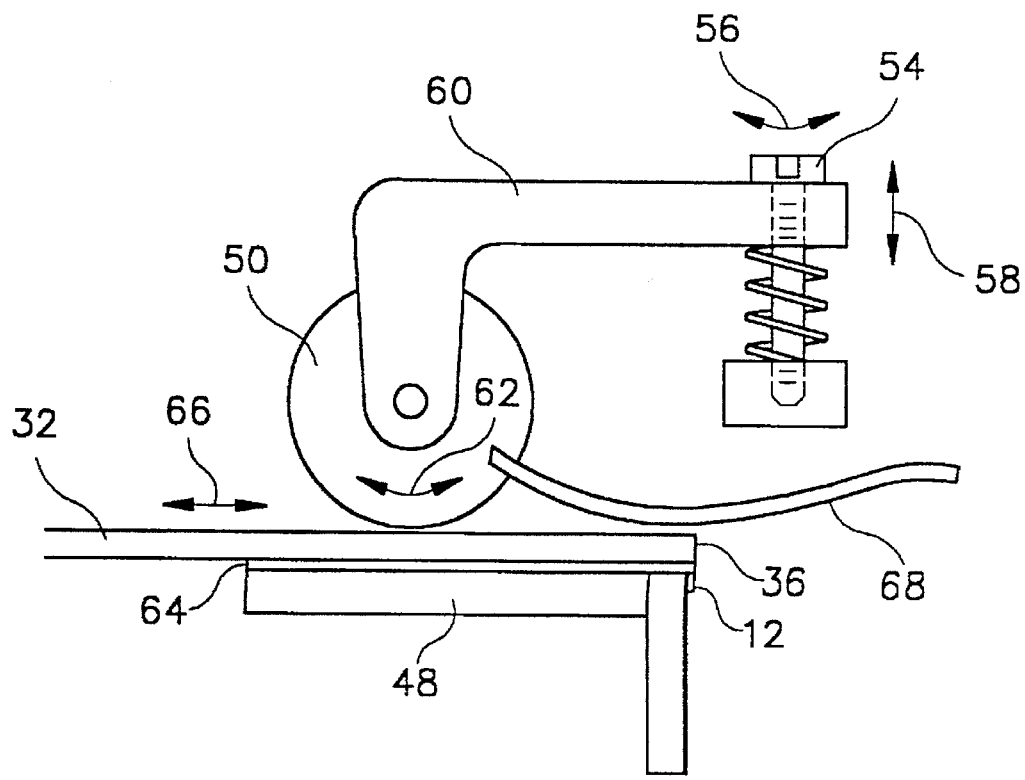
FIG. 6 is a drawing further illustrating the position of a magnetic film according to the practice of the invention.

The fixture 46 (FIG. 5) for positioning the film edge 36 in close proximity to MR 12 contains a TEFLON covered platen 48 on which the magnetic film 32 is placed. Drive wheels 50, 52 engage the magnetic film 32 on the platen 48, and movement of a spring loaded screw 54 threaded into a fixed portion of the fixture 46 allows very fine rotation of the drive wheels 50,52. Referring to FIG. 6, rotation 56 of the spring loaded screw 54 causes movement 58 of a handle 60 which results in fine rotation of the drive wheels, e.g. 50. The drive wheels, e.g. 50, contact the magnetic film 32 that rides on a TEFLON tape 64 secured to the platen 48 causing the magnetic film 32 to advance or recede along the direction 66. A BeCu spring 68 maintains the magnetic film in contact with the platen 48. The MR element 12 is fastened just forward of the platen 48, and by fine control of the screw 54, the edge 36 of the film 32 may be accurately positioned over the MR element 12.

The invention has been described in detail with particular reference to preferred embodiments thereof, but it will be understood that variations and modifications can be effected within the spirit and scope of the invention.

What is claimed is:

1. A method of measuring the remanence-thickness product of a magnetic material, comprising the steps of:

stationarily mounting a thin rectangular magnetoresistive (MR) element in a first plane, said MR element having a longitudinal edge;

stationarily mounting a short piece of thin, planar, magnetic material having an edge in a second plane perpendicular to said first plane of said MR element, said edge of said magnetic material being close to and above said edge of said MR element, said magnetic material being magnetized to saturation with its magnetization lying perpendicular to said magnetic material edge and in the plane of said magnetic material; and biasing said MR element to detect a magnetic field from said magnetic material, said magnetic field arising from the discontinuity in magnetic material magnetization occurring at said edge of said magnetic material, said edge being perpendicular to said magnetization.

2. The method of claim 1, wherein said biasing step includes providing a permanent magnet in said first plane adjacent to and longitudinally aligned with said MR element.

3. The method of claim 2 wherein said biasing step includes providing a second MR element in said first plane adjacent to but on the other side of said permanent magnet from said MR element, said second MR element being biased by said permanent magnet but being spaced far enough away from said magnetic material so as not to detect said magnetic field thereof; and further includes electrically connecting said MR element and said second MR element in a wheatstone bridge circuit, so that the output of said bridge circuit is proportional to the change in resistance of said MR element due only to the magnetic field of said magnetic material, with signal effects caused by common mode fields and thermal drift experienced by both MR elements being substantially canceled.

\* \* \* \* \*